US008476399B2

(12) United States Patent
Bolikal et al.

(10) Patent No.: US 8,476,399 B2
(45) Date of Patent: Jul. 2, 2013

(54) BIOCOMPATIBLE POLYMERS FOR MEDICAL DEVICES

(75) Inventors: Durgadas Bolikal, Edison, NJ (US); Don K. Brandom, La Mesa, CA (US); Lioubov Kabalnova, San Diego, CA (US); Ernest G. Baluca, San Diego, CA (US); Joachim Kohn, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/552,210

(22) Filed: Jul. 18, 2012

(65) Prior Publication Data

US 2013/0085238 A1 Apr. 4, 2013

Related U.S. Application Data

(63) Continuation of application No. 12/577,205, filed on Oct. 11, 2009, now Pat. No. 8,252,887.

(60) Provisional application No. 61/104,724, filed on Oct. 11, 2008, provisional application No. 61/104,728, filed on Oct. 11, 2008.

(51) Int. Cl.
*C08G 64/00* (2006.01)
*C08G 63/02* (2006.01)

(52) U.S. Cl.
USPC ........................................................ 528/206

(58) Field of Classification Search
USPC ........................................... 528/196, 198, 62
See application file for complete search history.

(56) References Cited

U.S. PATENT DOCUMENTS

| | | | |
|---|---|---|---|
| 3,636,956 A | 1/1972 | Schneider | |
| 3,663,515 A | 5/1972 | Hostettler et al. | |
| 4,744,365 A | 5/1988 | Kaplan et al. | |
| 4,747,956 A | 5/1988 | Kiniwa | |
| 4,822,829 A | 4/1989 | Muller et al. | |
| 4,980,449 A | 12/1990 | Kohn et al. | |
| 5,003,004 A | 3/1991 | Simms | |
| 5,066,772 A | 11/1991 | Tang et al. | |
| 5,099,060 A | 3/1992 | Kohn et al. | |
| 5,216,115 A | 6/1993 | Kohn et al. | |
| 5,219,564 A | 6/1993 | Zalipsky et al. | |
| 5,403,347 A | 4/1995 | Roby et al. | |
| 5,431,679 A | 7/1995 | Bennett et al. | |
| 5,587,507 A | 12/1996 | Kohn et al. | |
| 5,660,822 A | 8/1997 | Poiani et al. | |
| 5,665,831 A | 9/1997 | Neuenschwander et al. | |
| 5,670,602 A | 9/1997 | Kohn et al. | |
| 5,702,717 A | 12/1997 | Cha et al. | |
| 5,854,383 A | 12/1998 | Erneta et al. | |
| 5,916,998 A | 6/1999 | Ferruti et al. | |
| 5,952,450 A | 9/1999 | Ishihara et al. | |
| 6,120,491 A | 9/2000 | Kohn et al. | |
| 6,228,969 B1 | 5/2001 | Lee et al. | |
| 6,355,754 B1 | 3/2002 | Olson et al. | |
| 6,475,477 B1 | 11/2002 | Kohn et al. | |
| 6,592,899 B2 | 7/2003 | Fowers et al. | |
| 6,602,497 B1 | 8/2003 | Kohn et al. | |
| 6,943,214 B2 | 9/2005 | Flexman | |
| 7,166,134 B2 | 1/2007 | Datta et al. | |
| 7,169,187 B2 | 1/2007 | Datta et al. | |
| 7,479,157 B2 | 1/2009 | Weber et al. | |
| 2001/0046505 A1 | 11/2001 | Kohn et al. | |
| 2004/0082734 A1 | 4/2004 | Hatton et al. | |
| 2005/0106119 A1 | 5/2005 | Brandom et al. | |
| 2006/0024266 A1 | 2/2006 | Brandom et al. | |
| 2006/0034769 A1 | 2/2006 | Kohn et al. | |
| 2006/0034891 A1 | 2/2006 | Lawin et al. | |
| 2006/0036316 A1 | 2/2006 | Zeltinger et al. | |
| 2006/0178477 A1 | 8/2006 | Neuenschwander | |
| 2007/0117959 A1 | 5/2007 | Shastri et al. | |
| 2007/0231365 A1 | 10/2007 | Wang et al. | |
| 2007/0282435 A1 | 12/2007 | Wang et al. | |
| 2008/0063685 A1 | 3/2008 | Wang et al. | |
| 2008/0112999 A1 | 5/2008 | Baluca | |
| 2008/0146504 A1 | 6/2008 | Bonnin | |
| 2008/0152690 A1 | 6/2008 | Kohn et al. | |
| 2008/0187567 A1 | 8/2008 | Kohn et al. | |
| 2008/0243049 A1 | 10/2008 | Hardy | |
| 2008/0243228 A1 | 10/2008 | Wang et al. | |
| 2008/0269874 A1 | 10/2008 | Wang et al. | |
| 2009/0004243 A1 | 1/2009 | Pacetti et al. | |
| 2009/0035350 A1 | 2/2009 | Stankus et al. | |
| 2009/0088835 A1 | 4/2009 | Wang | |

FOREIGN PATENT DOCUMENTS

WO 9836013 A1 8/1998

OTHER PUBLICATIONS

Sousa, A., et al., "Selective Protein Adsorption on a Phase-Separated Solvent-Cast Polymer Blend", Langmuir, 22, 2006, pp. 6286-6292.
Tangpasuthadol, V., et al., "Thermal properties and physical ageing behaviour of tyrosine-derived polycarbonates", Biomaterials, 1996, vol. 17, No. 4., pp. 463-468.
Sarkar, D., et al., Structure-Property Relationship of L-Tyrosine-Based Polyurethanes for Biomaterial Applications, Journal of Applied Polymer Science, vol. 108, 2345-2355 (2008).
Polycarprolactone diol, 2011 obtained from the Sigma-Aldrich website: (http://www.sigmaaldrich.com/catalog/ProductDetail.do?D7=0&N5=SEARCH_CONCAT_PNO%7CBRAND_KEY&N4=189421% 7CALDRICH&N25=0&QS=ON&F=SPEC).
Nathan et al., Bio. Cong. Chem., 4, 54-62 (1993).
Nathan, Macromol., 25, 4476 (1992).
Dobrzynski et al. Structure-Property Relationships of Copolymers Obtained by Ring-Opening Polymerization of Glycolide and e-Caprolactone. Part 1. Synthesis and Characterization. Biomacromolecules 6(1): 483-488. 2005.

(Continued)

*Primary Examiner* — Terressa Boykin
(74) *Attorney, Agent, or Firm* — Fox Rothschild LLP

(57) ABSTRACT

The present invention relates to new classes of monomeric compounds, which may be polymerized to form novel biodegradable and bioresorble polymers and co-polymers. These polymers and co-polymers, while not limited thereto, may be adapted for radio-opacity and are useful for medical device applications and controlled release therapeutic formulations.

8 Claims, No Drawings

OTHER PUBLICATIONS

Teng et al., "Synthesis and characterization of poly(L-lactic acid)-poly(e-caprolactone) multiblock copolymers by melt polycondensation," Journal of Polymer Science Part A: Polymer Chemistry. 42: pp. 5045-5053, 2004. (Abstract).

Mligiliche et al., "Poly lactic acid-caprolactone copolymer tube with a denatured skeletal muscle segment inside as a guide for peripheral nerve regeneration: A morphological and electrophysiological evaluation of the regenerated nerves," Anatomical Science International, vol. 78, No. 3, Sep. 2003, pp. 156-161. (Abstract).

BIOCOMPATIBLE POLYMERS FOR MEDICAL DEVICES

CROSS-REFERENCE TO RELATED APPLICATIONS

This application is a continuation of Ser. No. 12/577,205, filed Oct. 11, 2009, which claims priority under 35 U.S.C. §119(e) to U.S. Provisional Patent Application Ser. Nos. 61/104,724 and 61/104,728, both of which were filed Oct. 11, 2008, and both of which are hereby incorporated by reference in their entirety for all purposes.

This application is also related to U.S. patent application Ser. No. 12/577,203 and U.S. Provisional Patent Application Ser. Nos. 61/250,548 and 61/250,550, all of which were filed on the same date of the present application. The disclosures of all three applications are hereby incorporated by reference in their entirety for all purposes.

FIELD OF THE INVENTION

The present invention relates to new classes of monomeric compounds, which may be polymerized to form novel biodegradable and bioresorble polymers and co-polymers. These polymers and co-polymers, while not limited thereto, may be adapted for radio-opacity and are useful for medical device applications and controlled release therapeutic formulations.

The present invention thus also relates to new biocompatible polymers suitable for use in implantable medical devices and monomers for such polymers. In particular, the present invention relates to polymers polymerized from monomer analogs of compounds that naturally occur in the human body and that contribute advantageous synthesis, processing and material properties to the polymers prepared therefrom.

BACKGROUND OF THE INVENTION

Diphenols are monomeric starting materials for polycarbonates, polyimino-carbonates, polyarylates, polyurethanes and the like. Commonly owned U.S. Pat. No. 5,099,060 discloses diphenolic monomers based on 3-(4-hydroxyphenyl) propionic acid and L-tyrosine alkyl esters (desaminotyrosyl-tyrosine alkyl esters). Subsequent related patents involve variations of this basic monomer structure, including halogenated radiopaque diphenolic monomers, such as the 3,5-di-iododesaminotyrosyl-tyrosine esters (I2DTX, wherein X=ester group, e.g., E=ethyl, H=hexyl, O=octyl, etc.) disclosed by U.S. Patent Application Publication No. 2006/0034769. The disclosures of both publications are incorporated by reference. Examples of other polymers suitable for various bioengineering applications include those described in U.S. Pat. No. 5,665,831; U.S. Pat. No. 5,916,998 and U.S. Pat. No. 6,475,477, along with the polymers described in U.S. Pat. Publication No. 2006/0024266, the disclosures of all of which are also incorporated by reference.

Although these monomers are useful in the synthesis of polymers for many medical implant applications, the rapidly evolving field of bioengineering has created a demand for a diverse library of different types of polymers offering a wide variety of choice of physical and mechanical properties. It is desirable that libraries of many different materials be available so that the specific polymer properties can be optimally matched with the requirements of the specific applications under development.

SUMMARY OF THE INVENTION

As set forth herein, the embodiments disclosed address these needs. Various embodiments provide polymer compositions derived from new monomers, medical devices containing such compositions, and methods of using such polymer compositions and devices.

New classes of monomeric compounds are provided, which may be polymerized to form novel polymers and co-polymers that, while not limited thereto, may be adapted for radio-opacity and are useful for medical device applications and controlled release therapeutic formulations, although not limited thereto. More specifically, the present invention introduces a novel class of monomers, which are polymerized to form polymers and copolymers with at least one or more aromatic repeating units that are analogs of compounds that naturally occur in the human body.

In one embodiment, copolymers are provided by reacting a hydroxyalkanoic acid or a sulfur or amino analog thereof having the structure of Formula Ia:

(1a)

with a hydroxyarylalkanoic acid or a hydroxyarylalkenoic acid or a sulfur or amino analog thereof having the structure of Formula Ib:

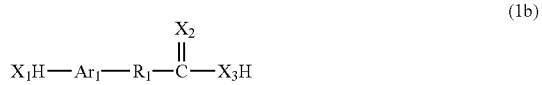

(1b)

wherein, $X_1$, $X_2$, $X_3$, $X_4$, $X_5$ and $X_6$ are independently selected from O, S and $NR_3$ wherein $R_3$ is selected from hydrogen and alkyl groups containing from one to six carbon atoms; $Ar_1$ is a phenyl ring,

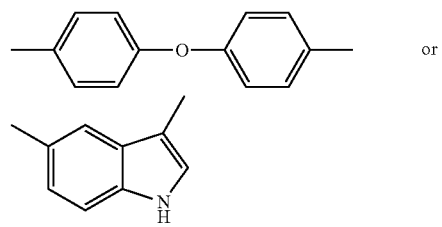

optionally substituted with from one to four substituents independently selected from a halogen, a halomethyl, a balomethoxy, a methyl, a methoxy, a thiomethyl, a nitro, a sulfoxide, and a sulfonyl; $R_1$ is selected from an optionally substituted alkyl group, an optionally substituted heteroalkyl group, an optionally substituted alkenyl group and an optionally substituted heteroalkenyl group, each containing from one to ten carbon atoms; $R_5$ and $R_6$ are independently selected from hydrogen and an alkyl group containing from one to six carbon atoms; and B is selected from an optionally substituted alkyl group containing from 1 to 18 carbons, an optionally substituted heteroalkyl group containing from 1 to 18 carbon atoms, an option-ally substituted alkenyl group containing from 1 to 18 carbon atoms and an optionally substituted heteroalkenyl group containing from 1 to 18 carbon atoms.

In one embodiment of formula Ia, each of $X_1$, $X_2$, $X_3$, $X_4$ and $X_5$ are all oxygen atoms and $Ar_1$ is substituted with at least one halogen atom. While not limited thereto, in accordance with the above, a ring of $Ar_1$ may be substituted with two halogen atoms (e.g. iodine or bromine), preferably, in positions ortho to $X_1$. Furthermore, $R_1$ may be an alkyl group containing from one to ten carbon atoms, with a preferred embodiment of two carbon atoms. Embodiments are also provided in which $R_1$ is a substituted with a lower alkyl group and a 4-hydroxyphenyl group so that Formula Ib includes compounds with the following structures:

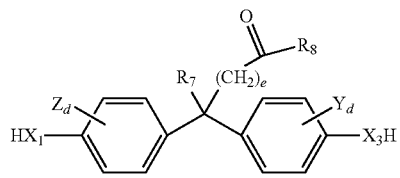

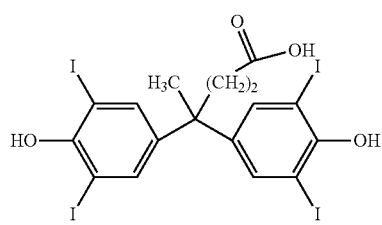

4,4-bis(4-hydroxy-3,5-diiodopheny)pentanoic acid

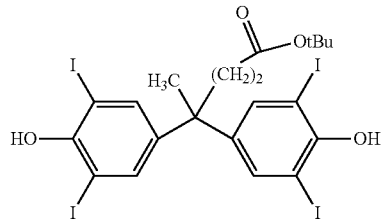

tert-butyl4,4-bis(4-hydroxy-3,5-diiodopheny)pentanoate wherein $X_1$ and $X_3$ are the same as previously described, $R_7$ is lower alkyl or $COOR_8$, $R_8$ is H, $C_1$-$C_{30}$ alkyl and $C_1$-$C_{30}$ heteroalkyl, Y and Z are independently iodine or bromine, and each d is independently 0, 1, 2, 3 or 4. In another embodiment $R_1$ is a substituted with a carboxyl group and a 4-hydroxyphenyl group so that Formula Ib includes compounds with the following structures

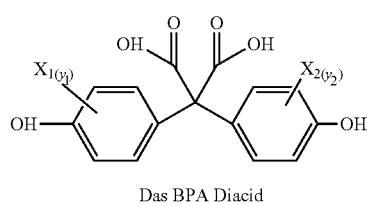

Das BPA Diacid

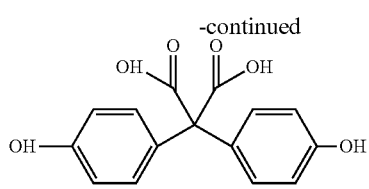

Chemical Formula: $C_{15}H_{12}O_6$
Molecular Weight: 288.25
Elemental Analysis C, 62.50; H, 4.20; O, 33.30

2,2-bis(4-hydroxyphenyl)malonic acid

Embodiments are provided in which B is a methylene group, and $X_4$ and $X_5$ are oxygen, wherein the Formula Ia monomer is glycolic acid and the resulting polymer is polyglycolic acid (PGA) copolymerized with the Formula Ib monomer. Embodiments are also included in which B is a methyl-substituted methylene group and $X_4$ and $X_5$ are oxygen, wherein the Formula Ia monomer is lactic acid and the resulting polymer is polylactic acid (PLA) copolymerized with the Formula Ib monomer. Both glycolic acid and lactic acid may be used, in which case the resulting polymer is poly(lactic-co-glycolic acid) (PLGA) copolymerized with the Formula Ib monomer. When the Formula Ib monomer is radio-opaque, embodiments are provided that are radio-opaque analogs of PGA, PLA and PLGA.

In further embodiments, aromatic monomer compounds are provided having the structure of formula IIa:

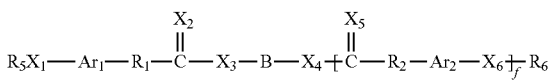

(IIa)

Wherein f is 0 or 1, $X_1$, $X_2$, $X_3$, $X_4$, $X_5$ and $X_6$ are independently selected from O, S and $NR_3$ wherein $R_3$ is selected from hydrogen and an alkyl group containing from one to six carbon atoms. $Ar_1$ and $Ar_2$ is each independently a phenyl ring,

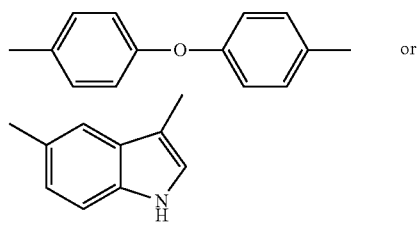

or optionally substituted with from one to four substituents independently selected from halogen, halomethyl, halomethoxy, methyl, methoxy, .thiomethyl, nitro, sulfoxide, and sulfonyl. $R_1$ and $R_2$ are independently selected from optionally substituted alkyl, heteroalkyl, alkenyl and heteroalkenyl groups each containing from one to ten carbon atoms. $R_5$ and $R_6$ are independently selected from hydrogen and an alkyl group containing from one to six carbon atoms. B is selected from a carboxy group, an optionally substituted alkyl group, an optionally substituted heteroalkyl group, an optionally substituted alkenyl group and an optionally substituted heteroalkenyl group, or B, $X_3$ and $X_4$ are selected so that $HX_3$—

B—X$_4$H defines a hydroxyl endcapped macromer, a mercapto endcapped macromer or an amine endcapped macromer.

The compounds of Formula IIa are prepared by reacting one mole of a compound having the structure HX$_3$—B—X$_4$H with either about one mole of the compound of Formula Ib (f=0) or about two moles of the compound of Formula Ib (f=1).

According to one embodiment, each of X$_1$, X$_2$, X$_3$, X$_4$, X$_5$, and X.6 is an oxygen atom. According to another embodiment, Ar$_1$ and Ar$_2$ are both independently substituted with at least one halogen atom. In another embodiment both Ar$_1$ and Ar$_2$ are ortho-substituted with two iodine atoms. Furthermore, R$_1$ may be an alkyl group containing from one to ten carbon atoms, with a preferred embodiment of two carbon atoms. In further embodiments, B is a methylene group or a methyl-substituted methylene group.

In one embodiment, the hydroxy endcapped macromer block comprises at least one macromer block selected from a hydroxy endcapped polycaprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone. In a further embodiment, the alkylene diol is hexane diol.

In one embodiment, the macromer dicarboxylate block comprises at least one macromer block selected from a polycaprolactone dicarboxylate, a polylactic acid dicarboxylate, a polyglycolic acid dicarboxylate, a poly(lactic acid-co-glycolic acid) dicarboxylate, a poly(alkylene diol) dicarboxylate, a poly(alkylene oxide) dicarboxylate and a polydioxanone dicarboxylate. In a further embodiment, the alkylene diol is hexane diol. The macromer block may be a homopolymer or the macromer block may be co-polymerized, for example, with phosgene, to form a carbonate macromer dicarboxylate.

When R$_5$ and R$_6$ of the Formula IIa compounds are alkyl, the compounds are not monomers but serve other potential end-uses where a non-reactive compound is desired, particularly when the compounds are radio-opaque.

Each of the foregoing compounds of Formula IIa may be adapted as a repeating unit in a polymeric composition having the structure of Formula IIb:

(IIb)

Wherein f is 0 or 1, X$_1$, X$_2$, X$_3$, X$_4$, X$_5$, X$_6$, X$_7$ X$_8$, R$_1$, R$_2$, R$_3$, R$_5$, R$_6$, Ar$_1$, Ar$_2$, B, B$_1$ and B$_2$, and the preferred species thereof, are the same as described above with respect to Formula IIa.

Polymers according to Formula IIb include block copolymers with a hydroxy endcapped macromer, a mercapto endcapped macromer or an amino endcapped macromer. In one embodiment, the hydroxy endcapped macromer block comprises at least one macromer block selected from a hydroxy endcapped polycaprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone. In a further embodiment, the alkylene diol is hexane diol. The macromer block may be a homopolymer or the macromer block may be copolymerized, for example with phosgene to form a hydroxy endcapped macromer carbonate.

While not limited thereto, macromer block copolymers of Formula IIb may have a molecular a weight ratio of polymer to hydroxy-capped macromer between about 25:75 and about 99:1.

The Formula Hb polymers also include polycarbonates, polyesters, polyphosphazines, polyphosphoesters and polyiminocarbonates. To this end, polymers having the structures of Formula IIb include polymers having the structure of Formula IIc:

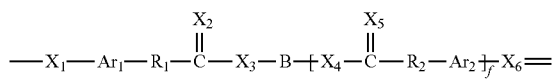

(IIc)

wherein D is selected from

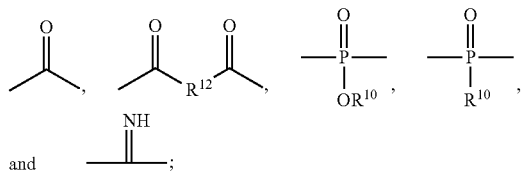

wherein R$^{10}$ is selected from H, an optionally substituted alkyl group, an optionally substituted heteroalkyl group, an optionally substituted alkenyl group and an optionally substituted heteroalkenyl group, each optionally crystallizable and containing from one to 30 carbon atoms, and R$^{12}$ is selected from an optionally substituted alkyl group, an optionally substituted heteroalkyl group, an optionally substituted alkenyl group and an optionally substituted heteroalkenyl group, each containing from one to 18 carbon atoms and an optionally substituted alkylaryl group, an optionally substituted heteroalkylaryl group, an optionally substituted alkenylaryl group and optionally substituted heteroalkenylary group, each containing from three to 12 carbon atoms.

D is additionally defined such that HX$_6$-D-X$_1$H defines an alkylene diol containing up to 24 carbon atoms, an alkylene diamine containing up to 24 carbon atoms, an alkylene dimercaptan containing up to 24 carbon atoms; or a hydroxy endcapped macromer, a mercapto endcapped macromer or an amine endcapped macromer as previously defined.

In accordance with another embodiment, monomeric compounds of any of the foregoing may be polymerized so as to form a polymer or co-polymer with repeating units of any one or more of these monomers. After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer thermoforming techniques such as extrusion and injection molding when the degradation temperature of the polymer is above the glass transition or crystalline melt temperature, or conventional non-thermal techniques can be used, such as compression molding, injection molding, solvent casting, spin casting, wet spinning. Combinations of two or more methods can be used. Shaped articles prepared from the polymers are useful, inter alia, as degradable biomaterials for medical implant applications.

In accordance with the discussion here, medical devices are provided comprising polymers disclosed herein, which are well-suited for use in producing a variety of resorbable medical devices or other implantable devices. Representative device embodiments include stents, disks, plugs, sutures, staples, clips, surgical adhesives, screws, anchors and the like. These and other similar implantable medical devices are preferably radiopaque, biocompatible, and have various times of bioresorption. To this end, the polymers may be further suitable for use in resorbable implantable devices with and without therapeutic agents, device components and/or coatings with and without therapeutic agents for use in other medical systems.

Other resorbable devices that can be advantageously formed from the polymers disclosed herein, and which serve as representative embodiments of useful medical devices, include devices for use in tissue engineering, dental applications, embolotherapy products for the temporary and therapeutic restriction or blocking of blood supply to treat tumors and vascular malformations, and controlled release therapeutic agent delivery devices, as discussed herein.

Another embodiment provides a method of treating a body lumen, by deploying within the body lumen a stent according to a medical device embodiment of the present invention.

Based on the foregoing, additional embodiments of the compounds, monomers, and polymers of the present invention are discussed herein and will be apparent to one of ordinary skill in the art.

DETAILED DESCRIPTION OF THE INVENTION

Novel classes of compounds, monomers, polymers and co-polymers are provided, polymerized from at least one or more repeatable units of an aromatic compound, which include compounds and analogs of compounds that naturally occur in the human body.

ABBREVIATIONS AND NOMENCLATURE

The following paragraphs provide definitions of various terms used herein.

As used herein, the terms "macromer," "macromeric" and similar terms have the usual meaning known to those skilled in the art and thus may be used to refer to oligomeric and polymeric materials that are functionalized with end groups that are selected so that the macromers can be copolymerized with other monomers. A wide variety of macromers and methods for making them are known to those skilled in the art. Examples of suitable macromers include hydroxy endcapped polylactic acid macromers, hydroxy endcapped polyglycolic acid macromers, hydroxy endcapped poly(lactic acid-co-glycolic acid) macromers, hydroxy endcapped polycaprolactone macromers, poly(alkylene diol) macromers, hydroxy endcapped poly(alkylene oxide) macromers and hydroxy endcapped polydioxanone macromers.

As used herein, the terms "polymer," "polymeric" and similar terms have the usual meaning known to those skilled in the art and thus may be used to refer to homopolymers, copolymers (e.g., random copolymer, alternating copolymer, block copolymer, graft copolymer) and mixtures thereof.

The term "thermal transition temperature" has the usual meaning known to those skilled in the art and thus may be used to refer to both first order thermal transitions and second order thermal transitions. The first order thermal transition of a polymer or phase thereof may be referred to herein as a "melting point" or Tm", and the second order thermal transition of a polymer or phase thereof may be referred to herein as a "glass transition temperature" or "Tg." Those skilled in the art will appreciate that a polymeric material or phase thereof may have exhibit either or both types of thermal transitions, as well as higher order thermal transitions. Thermal transition temperature may be determined by methods known to those skilled in the art, such as by DSC, DMA, DEA and TMA.

As used herein, the phrase "fracture toughness" means the resistance of a polymer under a static or dynamic load (or strain) to brittle failure from crack propagation within a glassy or semicrystalline phase.

The terms "radiopaque," "radio-opaque," "radiopacity," "radio-opacity," "radiopacifying" and similar terms have the usual meaning known to those skilled in the art and thus may be used to refer to polymer compositions that have been rendered easier to detect using medical imaging techniques (e.g., by X-ray and/or during fluoroscopy) being the incorporation of heavy atoms into the polymer composition. Such incorporation may be by mixing, e.g., by mixing an effective amount of a radiopacifying additive such as barium salt or complex, and/or by attachment of effective amounts of heavy atoms to one or more of the polymers in the polymer composition. For example, attachment of heavy atoms to a polymer in sufficient amounts may advantageously render the polymer easier to detect by various medical imaging techniques. The term "heavy atom" is used herein to refer to atoms having an atomic number of 17 or greater. Preferred heavy atoms have an atomic number of 35 or greater, and include bromine, iodine, bismuth, gold, platinum tantalum, tungsten, and barium. In certain configurations, polymer compositions may be inherently radiopaque. The term "inherently radiopaque" is used herein to refer to a polymer to which a sufficient number of heavy atoms are attached by covalent or ionic bonds to render the polymer radiopaque. This meaning is consistent with the under-standing of those skilled in the art, see, e.g., U.S. Patent Publication No. 2006/0024266, which is hereby incorporated by reference for all purposes, including for the particular purpose of describing radiopaque polymeric materials.

The terms "alkyl", "alkylene" and similar terms have the usual meaning known to those skilled in the art and thus may be used to refer to straight or branched hydro-carbon chain fully saturated (no double or triple bonds) hydrocarbon group. Terminal alkyl groups, e.g., of the general formula —$C_nH_{2n+1}$, may be referred to herein as "alkyl" groups, whereas linking alkyl groups, e.g., of the general formula —$(CH_2)_n$—, may be referred to herein as "alkylene" groups. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The alkyl group may be substituted or unsubstituted. When substituted, the substituent group(s) is (are) one or more group(s) individually and independently selected from lower alkyl, alkenyl, alkynyl, cycloalkyl, cycloalkenyl, cycloalkynyl, aryl, hydroxy-aryl, heteroaryl, heteroalicyclyl, aralkyl, heteroaralkyl, (heteroalicyclyl)alkyl, hydroxy, protected hydroxyl, alkoxy, aryloxy, acyl, carboxyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

The terms "alkenyl," "alkenylene" and similar terms have the usual meaning known to those skilled in the art and thus may be used to refer to an alkyl or alkylene group that contains in the straight or branched hydrocarbon chain one or more double bonds. An alkenyl group may be unsubstituted or substituted. When substituted the substituent(s) may be selected from the same groups disclosed above with regard to alkyl group substitution unless otherwise indicated.

The terms "heteroalkyl," "heteroalkylene" and similar terms have the usual meaning known to those skilled in the art and thus may be used to refer to an alkyl group or alkylene group as described herein in which one or more of the carbons atoms in the backbone of alkyl group or alkylene group has been replaced by a heteroatom such as nitrogen, sulfur and/or oxygen. Likewise, the term "heteroalkenylene" may be used to refer to an alkenyl or alkenylene group in which one or more of the carbons atoms in the backbone of alkyl group or alkylene group has been replaced by a heteroatom such as nitrogen, sulfur and/or oxygen.

The term "aryl" has the usual meaning known to those skilled in the art and thus may be used to refer to a carbocyclic (all carbon) monocyclic or multicyclic aromatic ring system that has a fully delocalized pi-electron system. Examples of aryl groups include, but are not limited to, benzene, naphthalene and azulene. The ring of the aryl group may have 5 to 50 carbon atoms. The aryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thio-carbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfon-amido, and amino, including mono- and di-substituted amino groups, and the protected derivatives thereof, unless the substituent groups are otherwise indicated. An aryl group substituted with alkyl may be referred to herein as "alkylaryl."

The term "heteroaryl" has the usual meaning known to those skilled in the art and thus may be used to refer to a monocyclic or multicyclic aromatic ring system (a ring system with fully delocalized pi-electron system) that contain(s) one or more hetero-atoms, that is, an element other than carbon, including but not limited to, nitrogen, oxygen and sulfur. The ring of the heteroaryl group may have 5 to 50 atoms. The heteroaryl group may be substituted or unsubstituted. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thia-diazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

The term "crystallizable" has the usual meaning known to those skilled in the art, see U.S. Patent Publication No. 20060024266, which is incorporated herein by reference for all purposes and particularly for the purpose of describing crystallizable groups. Polymers that contain crystallizable groups that are attached to the sides of the polymer, known as side chain crystallizable (SCC) polymers or "comb-like" polymers, are well-known, see N. A. Plate and V. P. Shibaev, J. Polymer Sci.: Macromol. Rev. 8:117-253 (1974), the disclosure of which is hereby incorporated by reference. In an embodiment, a polymer as described herein contains crystallizable side groups and thus may be regarded as a SCC polymer. It will be understood that the crystallizable side chains of SCC polymers are preferably selected to crystallize with one another to form crystalline regions and may comprise, for example, $-(CH_2)_x-$ and/or $-((CH_2)_b-O-)_y$ groups. The side chains are preferably linear to facilitate crystallization. For SCC polymers that contain $-(CH_2)_x$-groups in the crystallizable side chain, x is preferably in the range of about 6 to about 30, more preferably in the range of about 20 to about 30. For SCC polymers that contain $-((CH_2)_y-O-)_x$ groups in the crystallizable side chain, x is preferably in the range of about 6 to about 30 and y is preferably in the range of about 1 to about 8. More preferably, x and y are selected so that the $((CH_2)_y-O-)_x$ groups contain from about 6 to about 30 carbon atoms, even more preferably from about 20 to about 30 carbon atoms. The spacing between side chains and the length and type of side chain are preferably selected to provide the resulting SCC polymer with a desired melting point. As the spacing between side chains increases, the tendency for the side chains to be crystallizable tends to decrease. Likewise, as the flexibility of the side chains increases the tendency for the side chains to be crystallizable tends to decrease. On the other hand, as the length of the side chains increases, the tendency for the side chains to be crystallizable tends to increase. In many cases, the length of the crystallizable side chain may be in the range of about two times to about ten times the average distance between crystallizable side chains of the SCC polymer.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents.

Unless otherwise indicated, when a substituent is deemed to be "optionally substituted," or "substituted" it is meant that the substituent is a group that may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Similarly, the term "optionally ring-halogenated" may be used to refer to a group that optionally contains one or more (e.g., one, two, three or four) halogen substituents on the aryl and/or heteroaryl ring. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is hereby incorporated by reference in its entirety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z a mixture thereof. Likewise, all tautomeric forms are also intended to be included.

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

Polymer Compositions and Methods

An embodiment is provided in which the "X" groups and R$_1$ are selected so that the monomers and polymers are derivatives of hydroxy-arylalkanoic and hydroxy-aryl-alkenoic acids wherein the aryl group is a phenyl, phenoxyphenyl or indole ring. Examples of such acids include 4-hydroxycinnamic acid, 4-hydroxybenzoic acid, 2-(4-hydroxyphenyl) ethanoic acid, 3-(4-hydroxyphenyl)propanoic acid (desamino-tyrosine or DAT), 4-(4-hydroxyphenyl)butanoic acid, 5-hydroxy-1H-indol-3-yl-carboxylic acid, 2-(5-hydroxy-1H-indol-3-yl)ethanoic acid, 3-(5-hydroxy-1H-indol-3-yl)propanoic acid (5-hydroxy-desamino-tryptophan), 4-(5-hydroxy-1H-indol-3-yl)butanoic acid, 4-hydroxy-phenoxy-benzoic acid, 2-(4-hydroxy-phenoxy-phenyl)ethanoic acid, 3-(4-hydroxyphenoxy-phenyl)propanoic acid (desaminothyronine or DATH), 4-(4-hydroxy-phenoxy-phenyl)butanoic acid, and the like. Hydroxy-arylalkanoic acid and hydroxy-arylalkenoic acids from which monomers and polymers may be derived have the structure of Formula Ib, and compounds in which the "X" groups are all oxygens have the structure:

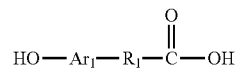

Wherein Ar$_1$ and R$_1$ and the preferred species thereof, are the same as described above with respect to Formula Ib.

Monomers and polymers derived from DAT, DATH and hydroxy-desamino-tryptophan are preferred, but not necessarily limiting to the present invention. In accordance with the foregoing, the DAT, DATH and tryptophan derivatives may be substituted at the phenyl ring position with a bromine or iodine, or any other similar element or compound adapted to provide for a radio-opaque quality.

According to an embodiment of the present invention, polyesters are provided, formed by self-condensation of the Formula Ib hydroxy-arylalkanoic acids and hydroxy-arylalkenoic acids, and having the structure of Formula IVb:

(IVb)

Wherein Ar$_1$ and R$_1$ and the preferred species thereof, are the same as described above with respect to Formula Ib, including embodiments wherein Ar$_1$ is a radio opaque phenyl, phenoxy-phenyl or indole ring and R$_1$ is an ethyl group. Sulfur and amino analogs of the Formula Ib monomers can be used to polymerize sulfur and amine analogs of the Formula IVb polymers.

The monomers of Formula Ib may be polymerized to form the polymers of Formula IVb utilizing any standard esterification reaction known in the art. Polyester block copolymer with any of the other embodiments discussed herein may also be prepared.

The advantageous physical properties of the DAT, DATH and hydroxy-desamino-tryptophan embodiments, in no particular order of importance, include the lack of a chiral center, so that, unlike amino acids, DAT, DATH and hydroxy-desamino-tryptophan do not give rise to enantiomers when coupled in the foregoing form. Also, because the COOH groups are not on a chiral carbon, there is no racemization during coupling to make the monomer. Furthermore, DAT, DATH and hydroxy-desamino-tryptophan are easier to iodinate than an aromatic amino acid, e.g. as tyrosine, when a radio-opaque polymer is desired. In addition, despite not being a compound naturally found in the body, DAT has low toxicity, attributable in part to being a closely-related analog of tyrosine, that is, DAT is tyrosine with the amino group removed. More significantly, DAT is an end stage metabolite, so that is there is no cause for concern that polymer degradation may convert DAT to toxic metabolites. The same advantages are also obtained by removing the amino groups from thyronine and tryptophan.

In addition to being non-toxic, the aromatic rings of DAT, DATH and hydroxy-desamino-tryptophan impart good mechanical properties to polymers. Removal of the amino groups gives better processing properties compared to amino acids.

One embodiment copolymerizes Formula Ia compounds with Formula Ib compounds. When the Formula Ia compound is a hydroxyalkanoic acid such as lactic acid or glycolic acid, and the Formula Ib compound is a hydroxy-arylalkanoic acid or a hydroxy-arylalkenoic acid, the two compounds are reacted in a polyesterification reaction using carbodiimide coupling agents or thionyl chloride or using acetic anhydride as follows:

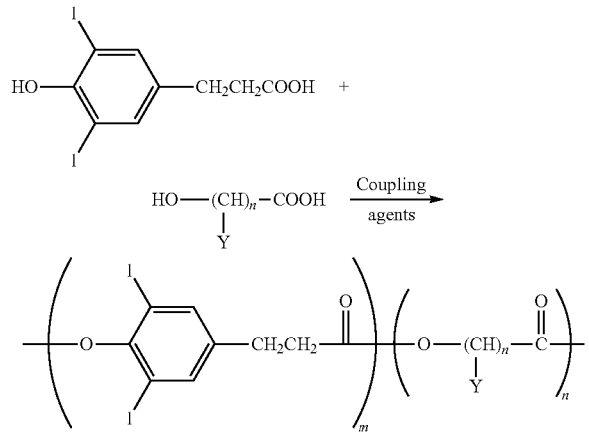

In the depicted embodiment the hydroxy-arylalkanoic acid is the radio-opaque 3,5-di-iodinated DAT monomer, referred to herein as I$_2$DAT, and Y is hydrogen or methyl so the hydroxyalkanoic acid is glycolic acid or lactic acid. When the hydroxy-arylalkanoic acid or hydroxy-arylalkenoic acid is radio-opaque, the ratio of m and n is selected to get the desired degree of radio-opacity. In the depicted embodiment, the resulting polymer is a radio-opaque PGA, PLA or PLGA copolymerized with I$_2$DAT. The molar quantity of m for any iodinated hydroxy-arylalkanoic acid or hydroxy-arylalkenoic acid, or sulfur or amino analog thereof, will range between about 5 and about 95 mol %. Embodiments also include molar quantities of m ranging between about 10 and about 65 mol %, between about 15 and about 60 mol %, between about 20 and about 55 mol %, between about 25 and about 50 mol % and between about 30 and about 45 mol %.

Formula IIa compounds are prepared by reacting either approximately one mole (f=0) or approximately two moles (f=1) of one or more Formula Ib compounds with approximately one mole of a compound having the structure of Formula Ic:

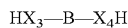 (Ic)

to provide a compound having the structure of Formula IIa:

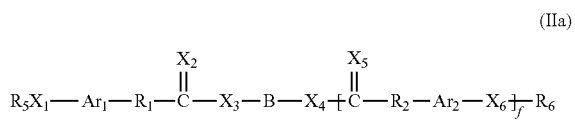 (IIa)

Wherein f, $X_1$, $X_2$, $X_3$, $X_4$, $X_5$, $X_6$, $R_1$, $R_2$, $R_3$, $R_5$, $R_6$, $Ar_1$, $Ar_2$, and B, and the preferred species thereof, are the same as previously described.

When the Formula Ib compound is a hydroxy-arylalkanoic acid, such as DAT, DATH or hydroxy-desamino-tryptophan, or a hydroxy-arylalkenoic acid, and the Formula Ic compound is a diol, the two compounds are reacted in an acid catalyzed Fischer Esterification reaction as follows:

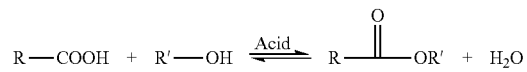

Because this reaction is reversible, removing water from the reaction mixture shifts the equilibrium to the right. Water removal is usually accomplished by way of azeotropic distillation; however other techniques known in the art may be employed as well. In instances where azeotropic distillation is desired, the solvent used for the reaction is carefully chosen so that it forms an azeotropic mixture with water. Generally, solvents such as toluene, heptane, chloroform, tetrachloethylene are preferred.

The main advantage of this reaction is that primary and secondary alcohols form esters with carboxylic acids under acid catalysis, whereas aromatic ring hydroxy groups are non-reactive under these conditions. Thus the carboxylic acid groups of Formula Ib, such as the 3-(4-hydroxyphenyl) propionic acid (DAT) and of 3-(3,5-diiodo-4-hydroxyphenyl) propionic acid (I$_2$DAT), can be reacted with primary or secondary alcohols while the phenolic groups remain intact. An example of the foregoing is as follows:

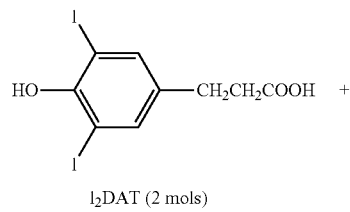

I$_2$DAT (2 mols)

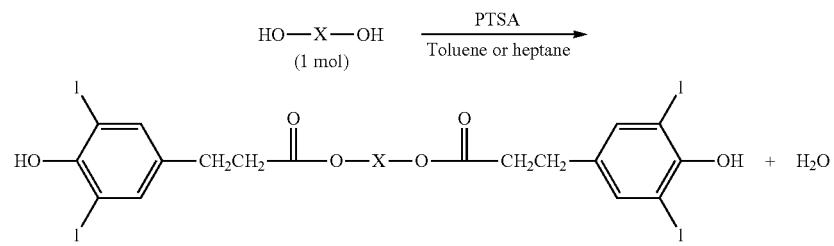

The X group in the foregoing is equivalent to the B group of Formula IIa, and may be any of the embodiments of B and the preferred species thereof. In the depicted embodiment, HO—X—OH can represent simple alkane diols such as 1,3-propane diol or macromer diols such as poly(ethylene glycol), hydroxy endcapped polycaprolactone-diol, hydroxy endcapped PLA, hydroxy endcapped PGA, hydroxy endcapped PLGA, etc.

When the Formula Ib compound is a hydroxy-arylalkanoic acid, such as DAT, DATH or hydroxy-desamino-tryptophan, or a hydroxy-arylalkenoic acid, the Formula IIa compounds contain diphenolic groups that can be polymerized, for example into polycarbonates by reaction with phosgene. When X in the depicted embodiment is PLA, PGA or PLGA, the polymer obtained is a radio-opaque copolymer of PLA, PGA or PLGA.

In certain embodiments, some of the macromer-diols such as hydroxy endcapped polycaprolactone-diol and poly(ethylene glycol) are commercially available. In some cases when such macromer diols as in the case poly(lactic acid)-diol were not available, they were prepared using an alkane diol as the initiator.

In further embodiments, B of Formula IIa is comprised of an macromeric alkyl group of a straight or branched chain alkyl group containing from 1 to 18 carbon atoms. In more specific embodiments, n is 3, 4, 5 or 6.

New Formula IIb polymers may be formed from the Formula IIa monomers of the present invention, in the same fashion as the desaminotyrosyl-tyrosine alkyl ester—derived polymers disclosed before. In one embodiment the Formula IIa diphenol monomers may be polymerized to form a polycarbonate, polyester, poly(phosphazine), poly(phosphoester) or poly(iminocarbonate). This embodiment may be represented by formula IIc:

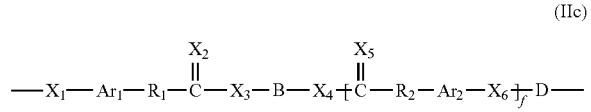

(IIc)

wherein each of $X_1$, $X_2$, $X_3$, $X_4$, $X_5$, $X_6$, $Ar_1$, $Ar_2$, $R^1$, $R^2$ and B, and the embodiments thereof, are the same as described above and D is selected from:

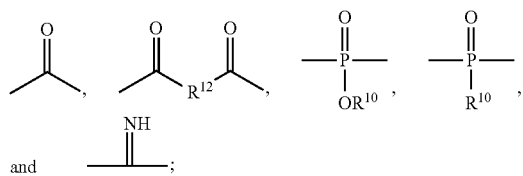

wherein $R^{10}$ is selected from H, an optionally substituted alkyl group, an optionally substituted heteroalkyl group, an optionally substituted alkenyl group and an optionally substituted heteroalkenyl group, each optionally crystallizable and containing from one to 30 carbon atoms, and $R^{12}$ is selected from an optionally substituted alkyl group, an optionally substituted heteroalkyl group, an optionally substituted alkenyl group and an optionally substituted heteroalkenyl group, each containing from one to 18 carbon atoms and an optionally substituted alkylaryl group, an optionally substituted heteroalkylaryl group, an optionally substituted alkenylaryl group and an optionally substituted heteroalkenylary group, each containing from three to 12 carbon atoms. One of ordinary skill in the art will understand that the placement of D in a position adjacent to $X_6$ is not limiting to the present invention and that D may also be positioned adjacent to $X_1$ to achieve similar effects, as discussed herein.

Based on the foregoing, in certain embodiments of Formula IIc, D is a carboxy group having the following structure:

wherein the carboxy group is derived from a phosgene starting material. This method is essentially the conventional method for polymerizing diols into polycarbonates. Suitable processes, associated catalysts and solvents are known in the art and are taught in Schnell, Chemistry and Physics of Polycarbonates, (Interscience, New York 1964), the teachings of which are incorporated herein by reference. Because $X_1$ and $X_6$ are independently selected from O, S and $NR_3$, the reaction of formula III monomers with phosgene may also produce urethane linkages (—$NR_3$—(C=O)—$NR_3$—), carbonodithioate linkages (—S—(C=O)—S—), carbamate linkages (—O—(C=O)—$NR_3$—), thiocarbonate linkages (—S—(C=O)—O—) and thiocarbamate linkages (—S—(C=O)—$NR_3$—). Other methods adaptable for use to prepare the poly-carbonate and other phosgene-derived polymers of the present invention are disclosed in U.S. Pat. Nos. 6,120,491 and 6,475,477 the disclosures of which are incorporated by reference.

In another embodiment, D of Formula IIc is a group having the structure:

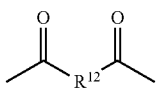

which is derived from a carboxylic acid starting material. When the monomer of Formula IIa is a diphenol, the Formula IIc polymer is formed by reaction of the diphenol with an aliphatic or aromatic dicarboxylic acids in the carbodiimide mediated process disclosed by U.S. Pat. No. 5,216,115 using 4-(dimethylamino) pyridinium-p-toluene sulfonate (DPTS) as a catalyst. The disclosure of U.S. Pat. No. 5,216,115 is incorporated by reference.

The foregoing process forms polymers with —O—C(=O)—$R_{12}$—C(=O)—O— linkages. $R_{12}$ may be selected so the dicarboxylic acids employed as starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid ($R_{12}$ may be —$CH_2$—$CH_2$—C(=O)—, —$CH_2$—$CH_2$—, —CH=CH— and —$CH_2$—C(=O)—, respectively).

Yet another naturally occurring aliphatic dicarboxylic acid is adipic acid ($R_{12}$ is (—$CH_2$—)$_4$), found in beet juice. Still another biocompatible aliphatic dicarboxylic acid is sebacic acid ($R_{12}$ is (—$CH_2$—)$_8$), which has been studied extensively and has been found to be nontoxic as part of the clinical evaluation of poly(bis(p-carboxyphenoxy)propane-cosebacic acid anhydride) by Laurencin et al., J. Biomed. Mater. Res., 24, 1463-81 (1990).

Other biocompatible aliphatic dicarboxylic acids include oxalic acid ($R_{12}$ is a bond), malonic acid ($R_{12}$ is —$CH_2$—), glutaric acid ($R_{12}$ is (—$CH_2$—)$_3$), pimelic acid ($R_{12}$ is (—$CH_2$—)$_5$), suberic acid ($R_{12}$ is (—$CH_2$—)$_6$) and azelaic acid ($R_{12}$ is (—$CH_2$—)$_7$). $R_{12}$ can thus represent (—$CH_2$—)$_Q$, where Q is between 0 and 8, inclusive. Among the suitable aromatic dicarboxylic acids are terephthalic acid, isophthalic acid and bis(p-carboxy-phenoxy) alkanes such as bis(p-carboxy-phenoxy) propane.

$R_{12}$ can also have the structure:

wherein a is 1, 2 or 3, inclusive, m is from 1 to 500,000, inclusive, and $R_{13}$ is hydrogen or a lower alkyl group containing from one to four carbon atoms. $R_{13}$ is preferably hydrogen, a is preferably 1, and m is preferably between about 10 and about 100, and more preferably between about 10 and about 50.

$R_{12}$ can also have the structure:

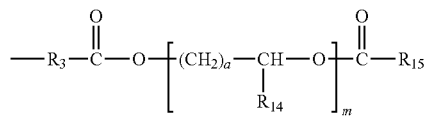

wherein a, m and $R_{14}$ and the preferred species thereof are the same as described above. $R_{15}$ is selected from a bond or straight and branched alkyl and alkylaryl groups containing up to 18 carbon atoms.

The following structures illustrates monomer compounds that are formed when $I_2$DAT diacetate of Formula Ib is reacted with phosgene:

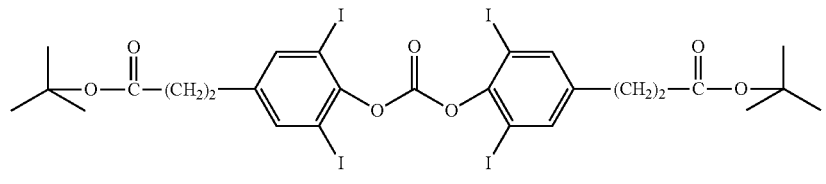

Chemical Formula: $C_{27}H_{30}I_4O_7$
Molecular Weight: 974.14
Elemental Analysis: C, 33.29; H, 3.10; I, 52.11; O, 11.50
tert-butyl 3,3'-(4,4'-carbonylbis(oxy)bis(3,5-diiodo-4,1-phenylene)dipropionate The other compounds of Formula Ib react similarly. Upon removal of the acetate groups the following dicarboxylic acid is obtained:

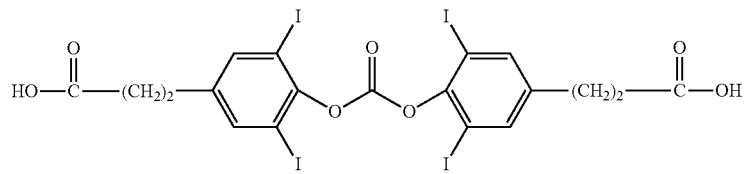

Chemical Formula: $C_{19}H_{14}I_4O_7$
Molecular Weight: 861.93
Elemental Analysis: C, 26.48; H, 1.64; I, 58.89; O, 12.99
3,3'-(4,4'-carbonylbis(oxy)bis(3,5-diiodo-4,1-phenylene)dipropanoic acid The depicted monomer compounds are dicarboxylates and have a structure depicted by Formula IIIa:

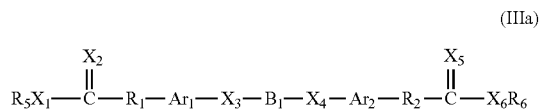

wherein $X_1$, $X_2$, $X_3$, $X_4$, $X_5$, and $X_6$ are independently selected from the group consisting of O, S and $NR_3$ wherein $R_3$ is selected from the group consisting of hydrogen and alkyl groups containing from one to six carbon atoms;

$Ar_1$ and $Ar_2$ are independently selected from the group consisting of phenyl,

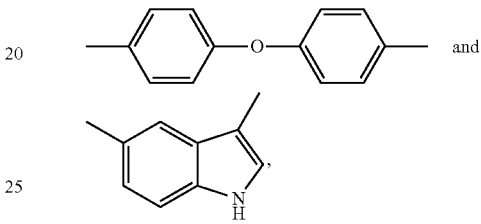

optionally substituted with from one to four substituents independently selected from the group consisting of halogen, halomethyl, halomethoxy, methyl, methoxy, thiomethyl, nitro, sulfoxide, and sulfonyl;

$R_1$ and $R_2$ are independently selected from the group consisting of an optionally substituted alkyl, heteroalkyl, alkenyl and heteroalkenyl groups containing from one to ten carbon atoms; $R_5$ and $R_6$ are independently selected from the group consisting of hydrogen and alkyl groups containing from one to six carbon atoms; and B is a carboxy group.

The Formula IIIa monomers are polymerized according to conventional dicarboxylate polymerization processes to form polyesters, polyamides, and the like, and the sulfur and amino analogs thereof, having the structure of Formula IIIB:

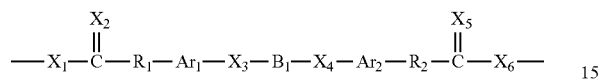

(IIIb)

wherein each of $X_1$, $X_2$, $X_3$, $X_4$, $X_5$, $X_6$, $Ar_1$, $Ar_2$, $R_1$, $R_2$ and B, and the embodiments thereof, are the same as described above for Formula Ma.

Polymers according to Formula IIb and Formula IIIb include block copolymers with a hydroxy endcapped macromer, a mercapto endcapped macromer or an amino endcapped macromer. Macromer blocks are selected that are also reactive with the co-monomer with which the Formula IIa or Formula IIIa monomer is being copolymerized. For example, a hydroxy endcapped macromer can be added to the reaction between a Formula IIa diphenol and phosgene to form a polycarbonate macromer block copolymer, or it can be added to the reaction between a Formula IIa diphenol and a dicarboxylic acid to form a polyarylate macromer block copolymer.

Molar fractions of macromer units range from greater than zero to less than one and are typically greater than zero up to about 0.5. Embodiments include an macromer molar fraction between about 0.10 and about 0.25.

Formula Ib includes bis-carboxylic acid monomer compounds that can be adapted to provide polymers among the embodiments disclosed herein having pendant free carboxylic acid groups:

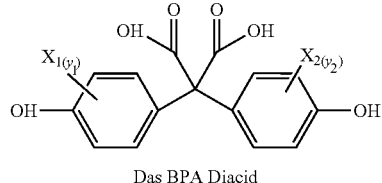

Das BPA Diacid

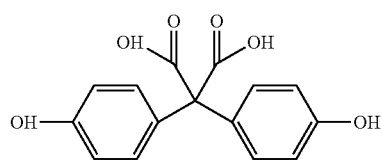

Chemical Formula: $C_{15}H_{12}O_6$
Molecular Weight: 288.25
Elemental Analysis: C, 62.50; H, 4.20; O, 33.30
2,2-bis(4-hydroxyphenyl)malonic acid

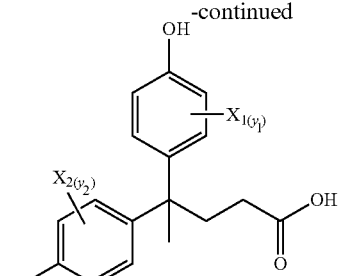

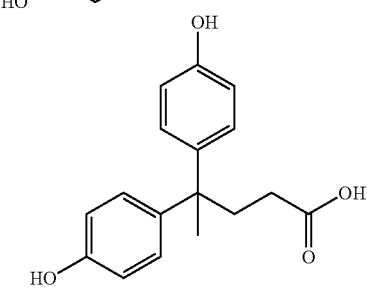

4,4-Bis(4-hydroxyphenyl)pentanoic acid
Journal of Pharmaceutical Sciences
Volume 56 Issue 10, Pages 1326-1328
Published Online: 17 Sep 2006
Synthesis of halogen substituted derivatives of
4,4-bis(4-hydroxyphenyl)pentanoic acid and
their antifungal properties
Rashmikant M. Patel, David P. Carew, John L. Lach It is difficult to prepare polymers with pendent free carboxylic acid groups by polymerization of corresponding monomers with pendent free carboxylic acid groups without cross-reaction of the free carboxylic acid group with the co-monomer. Accordingly, polymers having pendent free carboxylic acid groups are preferably prepared from the corresponding benzyl and tert-butyl ester polymers ($R_4$ is a benzyl or t-butyl group).

The benzyl ester polymers may be converted to the corresponding free carboxylic acid polymers through the selective removal of the benzyl groups by the palladium catalyzed hydrogenolysis method disclosed in U.S. Pat. No. 6,120,491, the disclosure of which is incorporated herein by reference, and particularly for the purpose of describing such methods. The tert-butyl ester polymers may be converted to the corresponding free carboxylic acid polymers through the selective removal of the tert-butyl groups by the acidolyis method disclosed in U.S. Patent Publication No. 20060034769, also incorporated herein by reference, and particularly for the purpose of describing such methods. The catalytic hydrogenolysis or acidolysis is preferable because the lability of the polymer backbone tends to discourage the employment of harsher hydrolysis techniques.

The molar fraction of free carboxylic acid units in the polymers described herein can be adjusted to modify the degradation of devices made from such polymers. For example, polymers with lower amounts of free carboxylic acid will tend to have longer lifetimes in the body. Further, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are desirable or required.

Polymers with a sufficient number of aromatic rings that are sufficiently substituted with bromine or iodine are inherently radiopaque. Various aromatic rings in both the first polymer phase and the second polymer phase can be iodine or bromine substituted. For example, independent of any particular polymer embodiment, the aromatic rings of the recurring units of the formula (I) may be substituted with at least one iodine or bromine atom, on at least one and preferably on both ring positions. In an embodiment, at least 50% of the aromatic rings of recurring units of the formula (I) in a polymer composition are substituted with from two to four iodine or bromine atoms.

The radiopaque monomers may be prepared according to the disclosure of U.S. Pat. No. 6,475,477, or the disclosure of U.S. Patent Publication No. 2006/0034769, the disclosures of both of which are incorporated herein by reference, and particularly for the purpose of describing such monomers and methods of making them. The iodinated and brominated phenolic monomers described herein can also be employed as radiopacifying, biocompatible non-toxic additives for biocompatible polymer compositions, as provided herein. Iodinated and brominated polymers may be polymerized from iodinate and brominated monomers, or the polymers can be iodinated or brominated after polymerization.

In another radiopaque polymer embodiment, methylene hydrogens are replaced with bromine or iodine to increase polymer radio-opacity. Such substitution may be concurrent with or in place of halogen substituted phenyl groups, as discussed above. Accordingly, radio-opaque polylactic acids, polyglycolic acids and polylactic-co-glycolic acids are provided by replacing a sufficient number of methylene hydrogens with bromine, iodine or both. A preferred radio-opaque polylactic acid contains lactic acid units with pendant tri-iodomethyl groups.

After polymerization of any of the foregoing compounds or monomers, appropriate work up of the polymers in accordance with preferred embodiments of the present invention may be achieved by any of a variety of known methods commonly employed in the field of synthetic polymers to produce a variety of useful articles with valuable physical and chemical properties.

Medical Uses

Various embodiments of the polymer compositions described herein, preferably derived from tissue compatible monomers, may be used to produce a variety of useful articles with valuable physical and chemical properties. The useful articles can be shaped by conventional polymer thermo-forming techniques such as extrusion and injection molding when the degradation temperature of the polymer is above the glass transition or crystalline melt temperature(s), or conventional non-thermal techniques can be used, such as compression molding, injection molding, solvent casting, spin casting, wet spinning.

Combinations of two or more methods can be used. Shaped articles prepared from the polymers are useful, inter alia, as biocompatible, biodegradable and/or bioresorbable biomaterials for medical implant applications.

In one embodiment, the medical device is a stent. It is contemplated that a stent may comprise many different types of forms. For instance, the stent may be an expandable stent. In another embodiment, the stent may be configured to have the form of a sheet stent, a braided stent, a self-expanding stem, a woven stent, a deformable stent, or a slide-and-lock stent. Stent fabrication processes may further include two-dimensional methods of fabrication such as cutting extruded sheets of polymer, via laser cutting, etch-ing, mechanical cutting, or other methods, and assembling the resulting cut portions into stents, or similar methods of three-dimensional fabrication of devices from solid forms.

In certain other embodiments, the polymers are formed into coatings on the surface of an implantable device, particularly a stent, made either of a polymer of the present invention or another material, such as metal. Such coatings may be formed on stents via techniques such as dipping, spray coating, combinations thereof, and the like. Further, stents may be comprised of at least one fiber material, curable material, laminated material, and/or woven material. The medical device may also be a stent graft or a device used in embolotherapy.

Details of stent products and fabrication in which the polymers disclosed herein may be employed are disclosed in US Pat. Publication No. 2006/0034769, the disclosure of which is incorporated by reference. Stents are preferably fabricated from the radiopaque polymers of the present invention, to permit fluoroscopic positioning of the device.

The highly beneficial combination of properties associated with the polymers disclosed herein means these polymers are well-suited for use in producing a variety of resorbable medical devices besides stents, especially implantable medical devices that are preferably radiopaque, biocompatible, and have various times of bioresorption. For example the polymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

The polymers described herein can thus be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lung-trachea/bronchus stents, and the like.

In addition, the resorbable polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that the resorbable polymers disclosed herein are well-suited for use in producing a variety of coatings for medical devices, especially implantable medical devices.

In some embodiments, the disclosed polymers may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices that can be advantageously formed from preferred embodiments of the polymers described herein include devices for use in tissue engineering. Examples of suitable resorbable devices include tissue engineering scaffolds and grafts (such as vascular grafts, grafts or implants used in nerve regeneration). The present resorbable polymers may also be used to form a variety of devices effective for use in closing internal wounds. For example biodegradable resorbable sutures, clips, staples, barbed or mesh sutures, implantable organ supports, and the like, for use in various surgery, cosmetic applications, and cardiac wound closures can be formed.

Various devices useful in dental applications may advantageously be formed from disclosed polymer embodiments. For example, devices for guided tissue regeneration, alveolar ridge replacement for denture wearers, and devices for the regeneration of maxilla-facial bones may benefit from being radiopaque so that the surgeon or dentist can ascertain the placement and continuous function of such implants by simple X-ray imaging.

Preferred embodiments of the polymers described herein are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which polymer embodiments described herein may be employed are disclosed in U.S. Patent Publication No. 2005/0106119, the dis-closure of which is incorporated by reference. Embolotherapy treatment methods are by their very nature local rather than systemic and the products are preferably fabricated from radiopaque polymers, such as the radiopaque polymers disclosed herein, to permit fluoroscopic monitoring of delivery and treatment.

The polymers described herein are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, taxinines, taxols, paclitaxel, dioxorubicin, cis-platin, adriamycin, and bleomycin. Non-limiting examples of preferred non-steroidal anti-inflammatory compounds include aspirin, dexamethasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimenta-tion. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, trans-poson, gene mutation, gene sequence, exon, intron, and, 3) "processed biologics", as used herein, such as cells, tissues or organs that have undergone manipulation. The thera-peutic agent may also include vitamin or mineral substances or other natural elements.

For devices placed in the vascular system, e.g., a stent, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of anti-proliferative agents, anti-inflammatory, anti-matrix metallo-proteinase, and lipid lowering, cholesterol modifying, anti-thrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the thera-peutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

In certain embodiments, any of the aforementioned devices described herein can be adapted for use as a therapeutic delivery device (in addition to any other functionality thereof). Controlled therapeutic delivery systems may be pre-pared, in which a therapeutic agent, such as a biologically or pharmaceutically active and/or passive agent, is physically embedded or dispersed within a polymeric matrix or physi-cally admixed with a polymer described herein. Controlled therapeutic agent delivery systems may also be prepared by direct application of the therapeutic agent to the surface of an implantable medical device such as a bioresorbable stent device (comprised of at least one of the polymers described herein) without the use of these polymers as a coating, or by use of other polymers or substances for the coating.

In certain embodiments, any of the aforementioned devices described herein can be adapted for use as a therapeutic delivery device (in addition to any other functionality thereof). Controlled therapeutic delivery systems may be pre-pared, in which a therapeutic agent, such as a biologically or pharmaceutically active and/or passive agent, is physically embedded or dispersed within a polymeric matrix or physi-cally admixed with a polymer embodiment. Controlled thera-peutic agent delivery systems may also be prepared by direct application of the therapeutic agent to the surface of an implantable medical device such as a bioresorbable stent device (comprised of at least one of the present polymers) without the use of these polymers as a coating, or by use of other polymers or substances for the coating.

The therapeutic agent may first be covalently attached to a monomer, which is then polymerized, or the polymerization may be performed first, followed by covalent attachment of the therapeutic agent. Hydrolytically stable conjugates are utilized when the therapeutic agent is active in conjugated form. Hydrolyzable conjugates are utilized when the thera-peutic agent is inactive in conjugated form.

Therapeutic agent delivery compounds may also be formed by physically blending the therapeutic agent to be delivered with the polymer embodiments using conventional tech-niques well-known to those of ordinary skill in the art. For this therapeutic agent delivery embodiment, it is not essential that the polymer have pendent groups for covalent attachment of the therapeutic agent.

The polymer compositions described herein containing therapeutic agents, regardless of whether they are in the form of polymer conjugates or physical admixtures of polymer and therapeutic agent, are suitable for applications where local-ized delivery is desired, as well as in situations where a systemic delivery is desired. The polymer conjugates and physical admixtures may be implanted in the body of a patient in need thereof, by procedures that are essentially conven-tional and well-known to those of ordinary skill in the art.

Implantable medical devices may thus be fabricated that also serve to deliver a therapeutic agent to the site of implan-tation by being fabricated from or coated with the therapeutic agent delivery system embodiment described herein in which a disclosed polymer embodiment has a therapeutic agent physically admixed therein or covalently bonded thereto, such as a drug-eluting stent. Covalent attachment requires a polymer to have a reactive pendant group. Embolotherapeutic particles may also be fabricated for delivery of a therapeutic agent.

Examples of biologically or pharmaceutically active thera-peutic agents that may be physically admixed with or covalently attached to polymer embodiments disclosed herein include acyclovir, cephradine, malphalen, procaine, ephedrine, adriamycin, daunomycin, plumbagin, atropine, quinine, digoxin, quinidine, biologically active peptides, chlorin e.sub.6, cephradine, cephalothin, proline and proline analogs such as cis-hydroxy-L-proline, malphalen, penicillin V and other antibiotics, aspirin and other non-steroidal anti-inflammatory compounds, nicotinic acid, chemodeoxycholic acid, chlorambucil, anti-tumor and anti-proliferative agents, including anti-proliferative agents that prevent restenosis, hormones such as estrogen, and the like. Biologically active compounds, for purposes of the present invention, are addi-tionally defined as including cell attachment mediators, bio-logically active ligands, and the like.

The invention described herein also includes various phar-maceutical dosage forms containing the polymer-therapeutic agent combinations described herein. The combination may be a bulk matrix for implantation or fine particles for admin-istration by traditional means, in which case the dosage forms include those recognized conventionally, e.g. tablets, cap-sules, oral liquids and solutions, drops, parenteral solutions and suspensions, emulsions, oral powders, inhalable solu-tions or powders, aerosols, topical solutions, suspensions, emulsions, creams, lotions, ointments, transdermal liquids and the like.

The dosage forms may include one or more pharmaceuti-cally acceptable carriers. Such materials are non-toxic to recipients at the dosages and concentrations employed, and include diluents, solubilizers, lubricants, suspending agents, encapsulating materials, penetration enhancers, solvents, emollients, thickeners, dispersants, buffers such as phos-phate, citrate, acetate and other organic acid salts, anti-oxi-dants such as ascorbic acid, preservatives, low molecular weight (less than about 10 residues) peptides such as pol-yarginine, proteins such as serum albumin, gelatin, or immu-noglobulins, other hydrophilic polymers such as poly(vi-nylpyrrolidinone), amino acids such as glycine, glutamic acid, aspartic acid, or arginine, monosaccharides, disaccha-rides, and other carbohydrates, including cellulose or its derivatives, glucose, mannose, or dextrines, chelating agents such as EDTA, sugar alcohols such as mannitol or sorbitol, counter-ions such as sodium and/or nonionic surfactants such as tween, pluronics or PEG.

Therapeutic agents to be incorporated in the polymer conjugates and physical admixture embodiments disclosed herein may be provided in a physiologically acceptable carrier, excipient stabilizer, etc., and may be provided in sustained release or timed release formulations supplemental to the polymeric formulation prepared in this invention. Liquid carriers and diluents for aqueous dispersions are also suitable for use with the polymer conjugates and physical admixtures.

Subjects in need of treatment, typically mammalian, using the disclosed polymer-therapeutic agent combinations, can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The polymer-therapeutic agent combinations may be prepared for storage under conditions suitable for the preservation of therapeutic agent activity as well as maintaining the integrity of the polymers, and are typically suitable for storage at ambient or refrigerated temperatures.

Depending upon the particular compound selected transdermal delivery may be an option, providing a relatively steady delivery of the drug, which is preferred in some circumstances. Transdermal delivery typically involves the use of a compound in solution with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

The polymer-drug formulation described herein may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally or via inhalation. Therapeutic agent toxicity could thus be reduced by selective delivery to the affected site. For example if the therapeutic agent is liposome encapsulated, and is injected intravenously, the liposomes used are taken up by vascular cells and locally high concentrations of the therapeutic agent could be released over time within the blood vessel wall, resulting in improved action of the therapeutic agent. The liposome encapsulated therapeutic agents are preferably administered parenterally, and particularly, by intravenous injection.

Liposomes may be targeted to a particular site for release of the therapeutic agent. This would obviate excessive dosages that are often necessary to provide a therapeutically useful dosage of a therapeutic agent at the site of activity, and consequent-ly, the toxicity and side effects associated with higher dosages.

Therapeutic agents incorporated into the polymers of described herein may desirably further incorporate agents to facilitate their delivery systemically to the desired target, as long as the delivery agent meets the same eligibility criteria as the therapeutic agents described above. The active therapeutic agents to be delivered may in this fashion be incorporated with antibodies, antibody fragments, growth factors, hormones, or other targeting moieties, to which the therapeutic agent molecules are coupled.

The polymer-therapeutic agent combinations described herein may also be formed into shaped articles, such as valves, stents, tubing, prostheses, and the like. Cardiovascular stents may be combined with therapeutic agents that prevent restenosis.

Implantable medical devices may be combined with therapeutic agents that prevent infection.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rates from the formulations of this invention are also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds of this invention may be administered several times daily, and other dosage regimens may also be useful.

In practicing the methods described herein, the polymer-therapeutic agent combinations may be used alone or in combination with other therapeutic or diagnostic agents. The compounds of this invention can be utilized in vivo, ordinarily in mammals such as primates such as humans, sheep, horses, cattle, pigs, dogs, cats, rats and mice, or in vitro.

An advantage of using the radiopaque, bioresorbable polymers described herein in therapeutic agent delivery applications is the ease of monitoring release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments the rate of therapeutic release from the degrading therapeutic delivery system will be correlated with the rate of polymer resorption. In such preferred embodiments, the straight-forward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and were used as received, unless otherwise indicated.

EXAMPLES

Example 1

Preparation of I₂DAT di-ester of 1,5-pentane diol

In a 500 mL flask equipped with overhead stirrer and a Dean-stark trap were placed 1,5-penatne diol (8.75 g, 84 mmol), I₂DAT (71 g, 0.17 mol), 4-toluenesulfonic acid (1.6 g, 8.4 mmol) and 200 mL of heptane. A nitrogen inlet adopter was placed on top of the condenser to maintain nitrogen atmosphere. The flask was heated using a heating mantle. The water collected was periodically measured and the reflux continued until the theoretical amount of water collected. More water than expected may be collected due to water present in the reagents. The reaction was stopped when the water evolution stopped (The heptane turned pink to purple due to trace quantities of iodine liberated). The reaction mixture is allowed to cool with stirring. The crude product is collected by filtration. For purification the crude is dissolved in 100 mL of acetone. To the solution was added with stirring 400 mL of 5% NaHCO₃ solution and stirring is continued until the product crystallizes. The product is collected by filtration and washed with 50 mL of 5% NaHCO₃ solution followed by 2×50 mL of DI water. The product was dried in a vacuum oven and characterized by $^1$H NMR and HPLC. Similar procedures were used to prepare I₂DAT di-esters of hexane diol and propane diol.

Example 2

Preparation of Poly(I₂DAT-LA)

In a 100 mL round-bottomed flask were placed 5 g (0.012 mol) of 3-(3,5-diiodo-4-hydroxyphenyl) propionic acid, 2.16 g (0.02 mol) of lactic acid, 1.41 g (0.008 mol) of dimethylaminopyridinium p-toluenesulfonate (DPTS) and 50 mL of methylene chloride. The contents of the flask were stirred under nitrogen and N,N'-diisopropylcarbodiimide (15 g, 0.12 mol) was added to the flask. The reaction mixture was stirred for 24 h under nitrogen. The reaction was stopped and the reaction mixture was filtered through a fritted glass funnel. The residue (diisopropyl urea) was discarded. The filtrate was precipitated with 250 mL isopropanol in a high speed blender, and triturated twice with 50 mL isopropanol. The precipitate was isolated and dried and dried in a vacuum oven. The polymer was characterized by $^1$H NMR, and GPC. The molecular weight GPC was 10,000.

Example 3

Preparation of Low Molecular Weight PLLA-Diol

In a 100 mL round bottom flask were placed 1,3-propanediol (1.02 g, 13.4 mmol), L-lactide (36.3 g, 252 mmol) and stannous octoate (0.5 g, 1.26 mmol). The contents of the flask were stirred and dried under vacuum. The flask was then lowered into a silicon oil bath whose temperature was maintained between 130-140° C. The lactide began to melt and a clear liquid resulted. When observed after 2 h the reaction mixture was opaque (white), still liquid at ca 130° C. The mixture was allowed to react for 24 h. On cooling a white solid was obtained. The $^1$H NMR showed the absence of unreacted 1,3-propane-diol. GPC with THF as mobile phase showed a bi-modal peak with a polystyrene equivalent Mn=3800; and Mw=7500.

Example 4

Polymerization of PLLA-Diol Using Triphosgene

In to a 250 mL round bottomed flask were added 7.50 g (0.005 mol) of PLLA-diol (Mn 1500). To the flask were also added 60 mL methylene chloride and 1.53 g (0.019 mol) pyridine and stirred with an overhead stirrer. To the resulting clear solution was slowly added over a period of 2 h, 0.42 g (0.006 equivalent of phosgene) triphosgene in 2 mL of methylene chloride, using a syringe pump. After stirring for 15 minutes, GPC showed a MW of 60,000. The reaction mixture was washed twice with 0.2 M HCl and precipitated with methanol. The initially formed viscous oil solidified after stirring for 1 hour into a white crystalline solid. This was dried in a vacuum oven at 40° C. for 24 h.

Example 5

Preparation of Iodinated PLLA-Diphenol with I₂Dat

In a 250 mL round bottomed flask equipped with a Dean-Stark trap were placed PLLA-diol (8.5 g, 5.0 mmol), I2DAT (4.60 g, 11 mol) 4-toluenesulfonic acid (0.1 g, 0.5 mmol) and toluene (125 mL). The reaction mixture was stirred using a magnetic stirrer and heated to reflux for 18 h. About 0.2 mL water collected in the Dean-Stark trap. The reaction mixture was allowed to cool and then evaporated to dryness. The residue was dissolved in 50 mL acetone. To this solution was added with stirring 200 mL 5% NaHCO3 solution and continued to stir for 1 h. The solid was isolated by filtration and washed with 50 mL 5% NaHCO3 solution and 2×50 mL Deionized water. The product was dried in a vacuum oven at 40° C. $^1$H NMR spectrum shows clearly the aromatic-H at 7.5 ppm, and the two methylene hydrogens of I₂DAT. Also the methane peak of the terminal group of PLLA (quartet at 4.35 ppm) reduced considerably showing that most of the diol reacted with I₂DAT.

Example 6

Preparation of Poly(PHMC2K Carbonate)

In a 1 L 4-necked flask with overhead stirrer were placed 53.4 g (27 mmol) of poly(hexamethylene carbonate 2000) (PHMC2K), 200 mL of methylene chloride and 8.23 g (0.104 mol) of pyridine. A clear solution formed on stirring. In a 20 mL sample bottle 2.33 g (24 mmol of phosgene) of triphosgene was dissolved in 8 mL of methylene chloride and added to the reaction flask over 2 h using the syringe pump. The reaction mixture was stirred for 15 m and then quenched with 250 mL of 9:1 mixture of THF-water. This was precipitated with 1500 mL of methanol in a beaker using overhead stirrer. The precipitate was allowed to settle for 1 hour, after which the supernatant was decanted off and discarded. The gluey precipitate at the bottom was washed with 200 mL methanol with stirring. It was then washed with 200 mL DI water. The residue was trans-ferred to a PTFE dish and dried under vacuum for 24 h at 50° C. (The product became a molten gel during drying and hardened on cooling). DSC showed an mp of 31.5° C.

Example 7

Monoester of Propane-Diol with I₂Dat

Into a 250 mL round-bottomed flask were added 14.4 g (190 mmol) 1,3-propanediol, 15.9 g (37.9 mmol) I₂DAT, 1.44 g (7.60 mmol) PTSA and 150 mL chloroform. The flask was equipped with a modified Dean-Stark trap used with solvents heavier than water. The contents of the flask were refluxed while stirring with a magnetic stirrer. The reaction was continued until the expected amount of water (about 0.8 mL) collected. The reaction mixture was evaporated to dryness and then stirred with 100 mL 5% $NaHCO_3$ soln. for 10 min and the aqueous layer was removed. This was repeated a total of 3 times followed by a wash with 100 mL deionized water. The product was isolated by filtration, washed with water, and dried in vacuum oven at 40° C. The dry product yield was 12.6 g (70%). HPLC of the product (yield 70%) showed it was a mixture of 93% of the desired product and 7% of the corresponding diester. The product was free of PTSA and $I_2DAT$.

Example 8

Synthesis of Desaminotyrosine Carbonate

In a 250 mL flask equipped with a magnetic stirrer was added desaminotyrosine (5 g). The starting material was dried and purged with nitrogen. Dry $CH_2Cl_2$ (50 mL) was syringed into the flask. Pyridine (10 mL) was syringed in and the reaction mixture was stirred to dissolve the starting material. The reaction mixture was cooled to 0° C. and then triphosgene (3.33 g) in 10 mL $CH_2Cl_2$ was added using a syringe pump over a 2 h period. The reaction was quenched by the addition of $THF/H_2O$ (1:1; 10 mL). The reaction was stirred for another 10 min and the volatiles were removed using a rotary evaporator. The crude product was precipitated by the addition of a mixture of ethyl acetate/hexanes. The product was characterized by $^1H$ NMR spectroscopy.

Example 9

Synthesis of di-ester of 1,3-propanediol with $I_2DAT$ (PrD-di $I_2DAT$)

Into a 500 mL round-bottomed flask equipped with an overhead stirrer, a Dean-Stark trap and a thermometer were added 3.04 g (0.040 mol) of 1,3-propanediol, 33.8 g (0.081 mol) of 3,5-diiododesaminotyrosyl tyrosine ethyl ester ($I_2DAT$), 0.76 g (4.0 mmol) of p-toluenesulfonic acid, and 200 mL of heptane. The flask was heated using a heating mantle, while stirring with the overhead stirrer so that heptane and water distilled over into the Dean-Stark trap. Heating continued until water collection stopped (about 1.45 mL water was collected). The reaction mixture was allowed to cool and the super-natant was removed by decantation. An off-white crude product was collected and dried.

Example 10

Purification of (PrD-di $I_2DAT$)

The crude (PrD-di $I_2DAT$) obtained above (95-97% pure by HPLC) was heated with 380 mL acetonitrile with stirring until the solid dissolved completely. The solution was allowed to cool in ice-water bath while stirring. The product precipitated as almost colorless powder, which showed purity of ca 98-99% by HPLC. For further purification the product was dissolved in acetonitrile (10 mL/g) and stirred with Norit (10 mg Norit/g of product). The hot solution was filtered to remove Norit and then cooled in an ice-water bath for recrystallization. A colorless powder was obtained (purity >99.5% by hplc). The product was dried in vacuum oven at 40° C. and had an m.p. of 88° C. (by DSC). Elemental analysis and $^1H$ NMR spectrum were in agreement with the structure.

Example 11

Polymerization of PrD-di $I_2DAT$ with PCL

Into a 1 L 4-necked round-bottomed flask equipped with a mechanical stirrer, an addition funnel, and a thermometer were added 50 g purified PrD-di $I_2DAT$ (85 wt. %), 4.71 g (8 wt. %) of polycaprolactone-diol (Mn=10,000), and 4.12 g (7 weight percent) of polycaprolactone-diol (Mn=1250). To the flask were then added 340 mL of methylene chloride and 26.5 mL of pyridine. On stirring a clear solution resulted to which a solution of 9.3 g of triphosgene in 28 mL of Methylene chloride was added over 2-3 h using the attached addition funnel. A viscous polymer solution resulted (Mw>200K). The polymer solution was quenched by the addition of a mixture of 31 mL of THF and 3 mL of water. After 15 min the quenched reaction mixture was precipitated with 600 mL of 2-propanol in a 4 L industrial blender. Repeated grinding with 2-propanol in the blender hardened the resulting oily precipitate. The product obtained in the form of powder was dried in a vacuum oven at 40° C. to constant weight. A number polymers were prepared by replacing PCL-diol of Mn 10,000 with PCL-diols of Mn=3,000, 5,500, and 8,500.

Example 12

4,4-bis(4-hydroxy-3,5-diiodopheny)pentanoic acid 4,4-bis(4-hydroxyphenyl)pentanoic acid (28.6 g, 0.1 mol) is dissolved in 250 mL 95% ethanol. To this solution is added 32 mL pyridine and 205 mL 2 M aqueous solution $KICl_2$ (0.41 mots) with stirring for 4 h. To the reaction mixture is added 1 L water and stirred for 2 h. The precipitated crude product is isolated by filtration and washed with water. For purification, the crude product is dissolved in water containing 17 g NaOH and the solution is filtered and acidified with conc. HCl, added with vigorous stirring. The obtained product is isolated by filtration and washed with several portions of water, dried under vacuum and characterized by hplc and elemental analysis.

Example 13

Preparation of Poly($I_2DAT$ Ester)

Into a 100 mL round bottomed flask were added 8.34 of $I_2DAT$, 4 g 4-dimethyl-aminopyridine-p-touleneic sulfonic acid salt, and 100 mL of dry chloroform and stirred when a suspention was obtained. To the stirred suspension was added 10 g diisopropyl carbodiimide and stirred for 4 h. GPC analysis of the reaction mixture gave oligomers with distribution ranging from 1000 to 20,000 daltons It will be understood by those of skill in the art that numerous and various modifications can be made without departing from the spirit of the present invention. Therefore, it should be clearly understood that the various embodiments of the present invention described herein are illustrative only and not intended to limit the scope of the present invention.

We claim:
1. A polymer comprising at least one repeating unit having the structure:

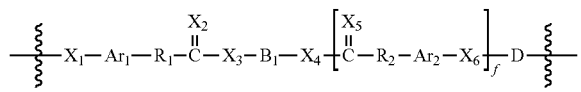

wherein, f is 0 or 1;

$X_1, X_2, X_3, X_4, X_5$, and $X_6$ are independently selected from the group consisting of O, S and $NR_3$ wherein $R_3$ is selected from the group consisting of hydrogen and alkyl groups containing from one to six carbon atoms;

$Ar_1$ and $Ar_2$ are independently selected from the group consisting of phenylene,

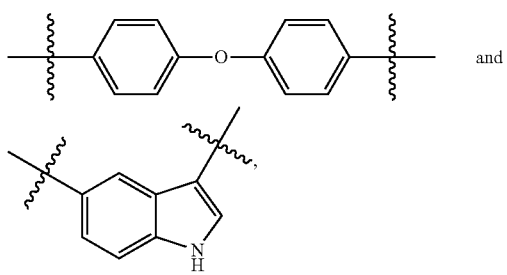

optionally substituted with from one to four substituents independently selected from the group consisting of halogen, halomethyl, halomethoxy, methyl, methoxy, thiomethyl, nitro, sulfoxide, and sulfonyl;

$R_1$ and $R_2$ are independently selected from the group consisting of optionally substituted alkylene, heteroalkylene, alkenylene and heteroalkenylene groups containing from one to ten carbon atoms; and $B_1$ is selected from the group consisting of a carbonyl group, optionally substituted alkylene groups of 1 to 18 carbon atoms, and groups having the structure:

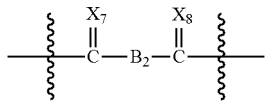

wherein $B_2$ is selected from the group consisting of optionally substituted alkylene, optionally substituted heteroalkylene, optionally substituted alkenylene and optionally substituted heteroalkenylene, or $B_2, X_3, X_4, X_7$ and $X_8$ are selected so that

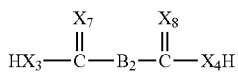

defines a capped macromer structure; and

D is selected from the group consisting of

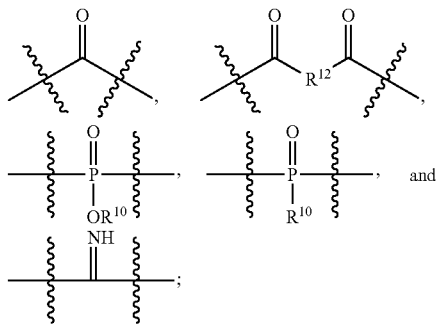

wherein $R^{10}$ is selected from the group consisting of H, saturated and unsaturated, substituted and unsubstituted alkyl, heteroalkyl, alkenyl and heteroalkenyl groups containing from one to 18 carbon atoms, and $R^{12}$ is selected from the group consisting of a bond, and saturated and unsaturated, substituted and unsubstituted alkylene, heteroalkylene, alkenylene and heteroalkenylene groups containing from one to 18 carbon atoms and alkylarylene, heteroalkylarylene, alkenylarylene and heteroalkenylarylene groups containing from three to 12 carbon atoms.

2. The polymer of claim 1, wherein said capped macromer structure is a macromer dicarboxylate.

3. The polymer of claim 1 wherein each $X_1, X_2, X_3, X_4, X_5$, and $X_6$ is an O atom.

4. The polymer of claim 3 wherein each of $Ar_1$ and $Ar_2$ is independently phenylene substituted with at least one halogen atom.

5. The polymer of claim 1 wherein D is a carbonyl group having the following structure:

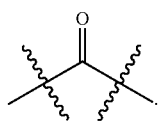

6. The polymer of claim 1 wherein D is a group having the structure:

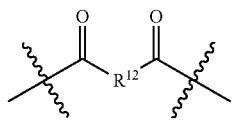

wherein $R^{12}$ is selected from the group consisting of a bond, and alkylene, heteroalkylene, alkenylene and heteroalkenylene groups containing from one to 18 carbon atoms.

7. The polymer of claim 1 wherein D is a heteroalkyl group having two carbonyl groups with an alkylene group spaced between the two carbonyl groups having up to 16 carbon atoms.

8. The polymer of claim 7 wherein the alkylene group spaced between the two carbonyl groups is comprised of two or four carbon atoms.

* * * * *